(12) United States Patent
Litz et al.

(10) Patent No.: US 7,663,301 B2
(45) Date of Patent: Feb. 16, 2010

(54) PORPHYRIN COMPOSITIONS

(75) Inventors: Kyle Erik Litz, Ballston Spa, NY (US); James Anthony Cella, Clifton Park, NY (US); Qing Ye, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 356 days.

(21) Appl. No.: 11/326,949

(22) Filed: Jan. 6, 2006

(65) Prior Publication Data

US 2006/0152149 A1 Jul. 13, 2006

Related U.S. Application Data

(60) Provisional application No. 60/643,077, filed on Jan. 11, 2005.

(51) Int. Cl.
*H01J 1/62* (2006.01)
*C08F 230/04* (2006.01)
*C07D 487/22* (2006.01)
*C07D 225/00* (2006.01)

(52) U.S. Cl. .................. 313/504; 526/241; 540/145; 540/465

(58) Field of Classification Search ............ 313/504; 526/241; 540/145, 465
See application file for complete search history.

(56) References Cited

U.S. PATENT DOCUMENTS 6,303,238 B1 10/2001 Thompson et al.

FOREIGN PATENT DOCUMENTS

| CN | 1631890 | 6/2005 |
|---|---|---|
| EP | 0 336 879 | 10/1989 |
| WO | WO 00/66528 | 11/2000 |
| WO | WO 02/066552 | 8/2002 |
| WO | WO 2004/008131 | 1/2004 |

OTHER PUBLICATIONS

Okura et al. "Photoinduced Hydrogen Evolution with Viologen Linked Porphyrin in a Micellar System" Bulletin fo the Chemical Society of Japan, 1986, vol. 59, pp. 3967-3968.*
Vollmer et al. "Anthryloligothienylporphyrins: Energy Transfer and Light-Harvesting Systems" Chemistry: A European Journal, 1998, vol. 4, No. 2, pp. 260-269.*
James B. Beil et al., "Synthesis of Nanosized "Cored" Star Polymers", American Chemical Society, Macromolecules, vol. 37, pp. 778-787, 2004.
International Search Report dated Jun. 29, 2006.
XP-002383211—James P. Collman et al., "Close Structural Analogues of the Cytochrome c Oxidase $Fe_{a3}/Cu_B$ Center Show Clean $4_e$—Electroreduction of $O_2$ to $H_2O$ at Physiological pH", Journal of the American Chemical Society, vol. 121, No. 6, pp. 1387-1388, 1999.
XP-002383212—Jin-Ook Baeg et al., "Covalently Supported Porphyrins as Ligands for the Preparation of Heme a3/$Cu_B$ Binuclear Active Site Analogues of Heme-Copper Terminal Oxidases and Metallation Under Mild Conditions", Chemical Comuunications, vol. 5, pp. 571-572, 1998.
XP-002383213—Diane L. Dick et al., "Molecular Encapsulation: Cyclodextrin-Based Analogues of Heme-Containing Proteins", Journal of the American Chemical Society, vol. 114, No. 7, pp. 2664-2669, 1992.
XP-002383442—Chemical Abstracts Service, Columbus, OH, Zao-Ying Li et al., "Synthesis of New Metalloporphyrins and Their Biological Activity as Mimics of Enzymes", Database Accession No. 2002:422107, pp. 1-15, 2002.
XP-002383216—Chemical Abstracts Service, Columbus, OH, Qilin Zhou et al., "Chiral Iron Porphyrin-Catalyzed Asymmetric Oxidation of Sulfides", Database Accession No. 1992:489903, 2 pages, 1992.
XP-002383625—Frank Würthner et al., "Synthesis and Energy Transfer Properties of Terminally Substituted Oligothiophenes", Journal of the American Chemical Society, vol. 117, No. 31, pp. 8090-8099, 1995.
Gerrit L'abbè et al, "Reactions of Acyl Isothiocyanates With 9-Diazofluorene: A Route To Macromolecules Having Pairs of Orthogonal Fluorene Groups", Journal of the Chemical Society Perkin Transactions 1, Database Accession No. BRN: 7506815, vol. 12, pp. 1349-1351, 1996.

* cited by examiner

*Primary Examiner*—Rebecca L Anderson
*Assistant Examiner*—Joseph R Kosack
(74) *Attorney, Agent, or Firm*—Mary Louise Gioeni

(57) ABSTRACT

Novel metal porphyrin compositions useful as organic phosphors are provided. The novel compositions are prepared from commercially available porphyrin-containing starting materials. In one instance a novel palladium-containing porphyrin composition having a number average molecular weight of greater than 12,000 grams per mole was prepared from 5,10,15,20-tetrakis(3',5'-di(hydroxy)phenyl)-21H-23H-porphyrin by reaction first with palladium(II) acetylacetonate, followed by reaction with 2-bromo-2-methylpropionyl bromide, and subsequent group transfer reaction of the alpha-bromo ester groups with 9,9-dioctyl-2-vinylfluorene in the presence of CuBr as a radical initiator. The product polymer exhibited a number average molecular weight of 12,884 grams per mole, a weight average molecular weight of 14,338 grams per mole, and a robust red phosphorescent emission. Porphyrin containing copoylmers comprising structural units derived from 9,9-dioctyl-2-vinylfluorene and 9-anthracenyl-methyl methacrylate were prepared in a similar fashion.

20 Claims, No Drawings

PORPHYRIN COMPOSITIONS

This is a Non-Provisional of currently pending U.S. provisional application No. 60/643,077, filed Jan. 11, 2005.

BACKGROUND

The invention relates to novel, metal-containing porphyrin heterocycles and methods for their preparation.

Metal-containing porphyrin heterocycles represent an important and useful class of organic compounds. Metal porphyrins are widely distributed in nature and play, in certain instances, important roles in various biological processes, such as photosynthesis. Synthetic metal-containing porphyrins are well known and have been used in inter alia studies of enzymatic catalysis and as useful catalysts in their own right.

Certain metal-containing porphyrin heterocycles have been shown to be useful as phosphorescent dopants in organic light-emitting devices. (See, for example, U.S. Pat. No. 6,303,238).

Although much has been learned in earlier work, there is nonetheless a need for new metal-containing porphyrin heterocycles which exhibit new or improved properties relative to known materials.

BRIEF DESCRIPTION

In one embodiment, the present invention provides a composition comprising a porphyrin heterocycle having structure I

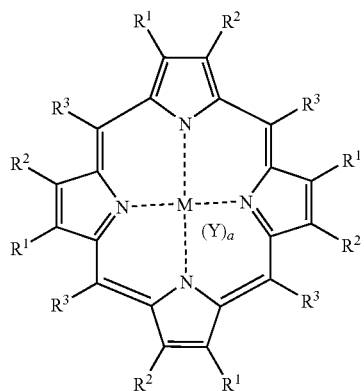

I wherein M is a divalent, trivalent or tetravalent metal ion; "a" is 0, 1, 2, or a non-zero fraction having a value between 0 and 1; Y is independently at each occurrence a charge balancing counterion; $R^1$ and $R^2$ are independently at each occurrence a halogen, a $C_1$-$C_{20}$ aliphatic radical, a $C_3$-$C_{20}$ cycloaliphatic radical, a $C_2$-$C_{20}$ aromatic radical, or $R^1$ and $R^2$ may together form a divalent aliphatic radical, a divalent cycloaliphatic radical, or a divalent aromatic radical; $R^3$ is independently at each occurrence an organic radical having structure II

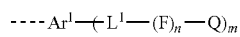

II wherein $Ar^1$ is a $C_2$-$C_{50}$ aromatic radical; $L^1$ is a $C_1$-$C_{20}$ aliphatic radical, a $C_3$-$C_{20}$ cycloaliphatic radical, or a $C_2$-$C_{20}$ aromatic radical; F is independently at each occurrence a structural unit derived from an olefin monomer selected from the group consisting of polycyclic olefin monomers and heterocyclic olefin monomers; "n" is independently at each occurrence an integer from 1 to about 200;

Q is independently at each occurrence a hydrogen, a halogen, a $C_1$-$C_{20}$ aliphatic radical, a $C_3$-$C_{20}$ cycloaliphatic radical, or a $C_2$-$C_{20}$ aromatic radical; and "m" is independently at each occurrence an integer from 1 to about 10.

In another embodiment, the present invention provides an organic phosphor comprising a porphyrin heterocycle having structure I.

In yet another embodiment, the present invention provides a method of making a composition comprising a porphyrin heterocycle having structure I, the method comprising contacting in the presence of an initiator a heterocyclic precursor compound having structure XVII

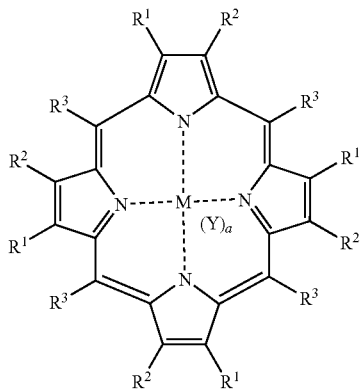

XVII wherein M is a divalent, trivalent or tetravalent metal; "a" is 0, 1, 2, or a non-zero fraction having a value between 0 and 1; Y is independently at each occurrence a charge balancing counterion; $R^1$ and $R^2$ are independently at each occurrence a halogen, a $C_1$-$C_{20}$ aliphatic radical, a $C_3$-$C_{20}$ cycloaliphatic radical, a $C_2$-$C_{20}$ aromatic radical, or $R^1$ and $R^2$ may together form a divalent aliphatic radical, a divalent cycloaliphatic radical, or a divalent aromatic radical; $R^3$ is independently at each occurrence an organic radical having structure XVIII

XVIII wherein $Ar^1$ is a $C_2$-$C_{50}$ aromatic radical; $L^1$ is a $C_1$-$C_{20}$ aliphatic radical, a $C_3$-$C_{20}$ cycloaliphatic radical, or a $C_2$-$C_{20}$ aromatic radical; Q is halogen susceptible to group transfer, a $C_1$-$C_{20}$ aliphatic radical susceptible to group transfer, a $C_3$-$C_{20}$ cycloaliphatic radical susceptible to group transfer, or a $C_2$-$C_{20}$ aromatic radical susceptible to group transfer; and "m" is an integer from 1 to about 10;

with at least one olefin monomer selected from the group consisting of polycyclic olefin monomers and heterocyclic olefin monomers.

DETAILED DESCRIPTION

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "organic" includes organometallic compounds. Thus, the phosphorescent metal-containing porphyrin compositions provided by the present invention fall within the scope of the term "organic phosphors".

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having $4n+2$ "delocalized" electrons where "n" is an integer equal to 1 or greater, as illustrated by phenyl groups ($n=1$), thienyl groups ($n=1$), furanyl groups ($n=1$), naphthyl groups ($n=2$), azulenyl groups ($n=2$), anthraceneyl groups ($n=3$) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component $-(CH_2)_4-$. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., $-OPhC(CF_3)_2PhO-$), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., $-OPhC(CN)_2PhO-$), 3-methylphen-1-yl, methylenebis(4-phen-1-yloxy) (i.e., $-OPhCH_2PhO-$), 2-ethylphen-1-yl, phenylethenyl, 3-formyl-2-thienyl, 2-hexyl-5-furanyl, hexamethylene-1,6-bis(4-phen-1-yloxy) (i.e., $-OPh(CH_2)_6PhO-$), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2-$) represents a $C_3$ aromatic radical. The benzyl radical ($C_7H_7-$) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2-$) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., $-C_6H_{10}C(CF_3)_2C_6H_{10}-$), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., $-OC_6H_{10}C(CN)_2C_6H_{10}O-$), 3-methylcyclohex-1-yl, methylenebis(cyclohex-4-yloxy) (i.e., $-OC_6H_{10}CH_2C_6H_{10}O-$), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}O$—), 4-mercaptomethylcyclohex-1-yl (i.e., 4-$HSCH_2C_6H_{10}O$—), 4-methylthiocyclohex-1-yl (i.e., 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g., $(CH_3O)_3SiCH_2CH_2C_6H_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

As noted, in one aspect the present invention provides a composition comprising porphyrin heterocycle I. In structure I, the metal M may be any metal ion which can insert into the interior cavity of the porphyrin. In one embodiment, M is a divalent metal ion, for example $Pd^{2+}$ or $Pt^{2+}$. In another embodiment, M is a trivalent metal ion, for example $Fe^{3+}$ or $Co^{3+}$. In yet another embodiment, M is a tetravalent metal ion, for example $Ti^{+4}$. Those skilled in the art will appreciate that when M is a metal ion having a charge greater than +2, one or more charge balancing counterions Y will be present to preserve a net charge of zero for the system. The charge balancing counterion Y may be any anion. Those skilled in the art will understand that when the charge balancing counterion is a polyvalent anion such as the dianion of malonic acid, the anion may associate with one or more metal ions depending on the charge of the metal ion. This point is illustrated by way of the following examples. When M is $Fe^{3+}$ and Y is acetate ($CH_3CO_2^-$) the charge on the metal will be balanced by a single acetate anion for each molecule having structure I and the value of "a" will be 1. Alternatively, suppose M is $Fe^{3+}$ and Y is the dianion of malonic acid ($^-O_2CCH_2CO_2^-$), only a single additional negative charge is needed to balance the overall charge of the heterocycle I and thus the value of "a" will be a fraction (½). In such a case, the polyvalent anion (malonate) will be associated with two molecules of the porphyrin heterocycle. In certain embodiments, the value of "a" will be zero, 1 or 2. As noted with the example just cited, however, fractional values of "a" between 0 and 1 are also possible. Thus, "a" is defined as 0, 1, 2, or a non-zero fraction having a value between 0 and 1.

The groups $R^1$ and $R^2$ are, as noted, independently at each occurrence a halogen, a $C_1$-$C_{20}$ aliphatic radical, a $C_3$-$C_{20}$ cycloaliphatic radical, a $C_2$-$C_{20}$ aromatic radical, or $R^1$ and $R^2$ may together form a divalent aliphatic radical, a divalent cycloaliphatic radical, or a divalent aromatic radical. Structures Ia-Ie in Table 1 illustrate various embodiments of the present invention wherein the groups $R^1$ and $R^2$ are varied. For the purpose of fully illustrating of these non-limiting examples, in structures Ia-Ie; M is $Pd^{2+}$, "a" is zero, and $R^3$ (discussed in detail hereinafter) is the group —$Ar^1(L^1(F)_nQ)_m$ wherein $Ar^1$ has structure XII (discussed in detail hereinafter), $L^1$ has structure XIII (discussed in detail hereinafter), F is a moiety derived from 9,9-dioctyl-2-vinylfluorene, "n" is 5, Q is Br, and "m" is 2. Thus, each of the examples Ia-Ie represents a single and unique species of the present invention. Those skilled in the art will understand that the embodiment Ic represents a case in which $R^1$ and $R^2$ together form a divalent aliphatic radical (—$(CH_2)_6$—). Similarly, those skilled in the art will understand that the embodiments Id and Ie represent cases in which $R^1$ and $R^2$ together form a divalent aromatic radical (—$(CH_2)_3$CHPh-) and a divalent cycloaliphatic radical (—$(CH_2)_3$CHcyclohexyl-) respectively.

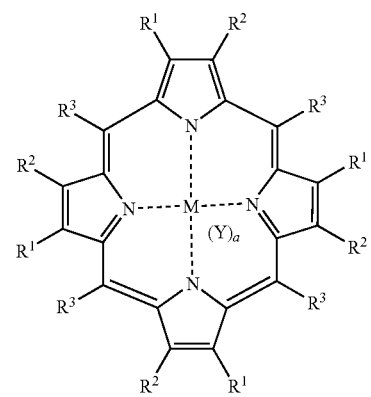

I

TABLE 1

ILLUSTATIVE VARIATIONS IN $R^1$ AND $R^2$

| Entry | Structure $R^1$ | Structure $R^2$ |
|---|---|---|
| Ia | Et | Et |
| Ib | H | Et |
| Ic | ----CH$_2$CH$_2$CH$_2$---- | ----CH$_2$CH$_2$CH$_2$---- |
| Id | ----CH$_2$CH$_2$CH$_2$---- | 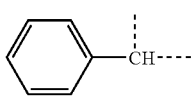 |
| Ie | ----CH$_2$CH$_2$CH$_2$---- | 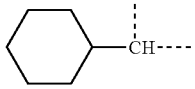 |

As noted, $R^3$ is independently at each occurrence an organic radical having structure II

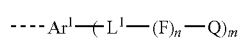

wherein wherein $Ar^1$ is a $C_2$-$C_{50}$ aromatic radical; $L^1$ is a $C_1$-$C_{20}$ aliphatic radical, a $C_3$-$C_{20}$ cycloaliphatic radical, or a $C_2$-$C_{20}$ aromatic radical; F is independently at each occurrence a structural unit derived from an olefin monomer selected from the group consisting of polycyclic olefin monomers and heterocyclic olefin monomers;

"n" is independently at each occurrence an integer from 1 to about 200;

Q is independently at each occurrence a hydrogen, a halogen, a $C_1$-$C_{20}$ aliphatic radical, a $C_3$-$C_{20}$ cycloaliphatic radical, or a $C_2$-$C_{20}$ aromatic radical; and "m" is independently at each occurrence an integer from 1 to about 10.

The group $Ar^1$ is an aromatic radical which is at least divalent, the group $Ar^1$ being attached to both the porphyrin core and the pendant group(s) ($L^1(F)_nQ$). In one embodiment, the group $R^3$ is elaborated from the reaction of a porphyrin ring system bearing reactive pendant groups. For example, the condensation of pyrrole with 4-hydroxybenzaldehyde affords after treatment with a source of palladium ions (e.g. palladium acetylacetonate) a metal-containing heterocycle having structure I wherein M is Pd$^{2+}$, "a" is 0, $R^1$ and $R^2$ are hydrogen, and $R^3$ is the 4-hydroxyphenyl radical. Thus, the $Ar^1$ group present in various embodiments of the present invention may be derived from any suitably functionalized aromatic aldehyde, for example 4-hydroxybenzaldehyde, 4-carboxybenzaldehyde, 3,5-dihydroxybenzaldehyde, 3,5-carboxybenzaldehyde, and the like. The other moieties present in $R^3$ in various embodiments of the invention, $L^1$, F, and Q may be attached via the functional group of the suitably functionalized aromatic aldehyde as discussed hereinafter.

In one embodiment, the group $Ar^1$ present in structure II is a divalent aromatic radical having structure XI

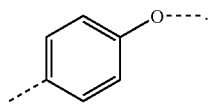

In an alternate embodiment, the group $Ar^1$ present in structure II is a trivalent aromatic radical having structure XII.

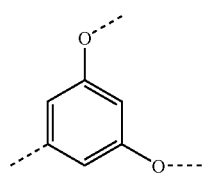

It should be noted (with continued reference to structure II), that when $Ar^1$ is a trivalent aromatic radical having structure XII, the group $Ar^1$ bears two pendant groups ($L^1(F)_nQ$) and "m" has a value of 2.

The group $L^1$ is independently at each occurrence a divalent $C_1$-$C_{20}$ aliphatic radical, a divalent $C_3$-$C_{20}$ cycloaliphatic radical, or a divalent $C_2$-$C_{20}$ aromatic radical. In one embodiment, $L^1$ is a divalent aliphatic radical having structure XIII.

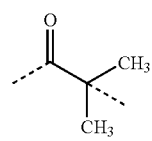

The group F is independently at each occurrence a structural unit derived from an olefin monomer selected from the group consisting of polycyclic olefin monomers and heterocyclic olefin monomers. Polycyclic olefin monomers are olefin monomers comprising at least two ring structures and are illustrated by polycyclic olefin monomers III, IV, V, and VI

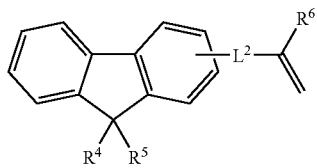

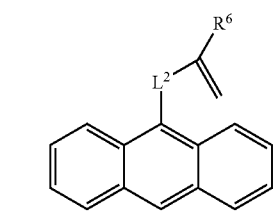

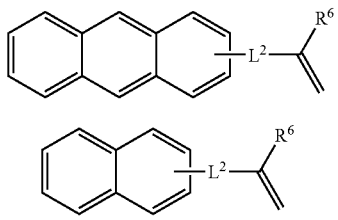

V

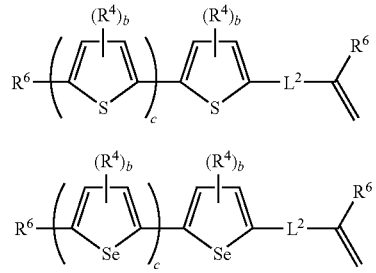

IX

VI

X wherein $R^4$ and $R^5$ are independently hydrogen, a $C_1$-$C_{20}$ aliphatic radical, a $C_3$-$C_{20}$ cycloaliphatic radical, or a $C_2$-$C_{20}$ aromatic radical; L is a bond, a $C_1$-$C_{20}$ aliphatic radical, a $C_3$-$C_{20}$ cycloaliphatic radical, or a $C_2$-$C_{20}$ aromatic radical; and $R^6$ is hydrogen, halogen, a $C_1$-$C_{20}$ aliphatic radical, a $C_3$-$C_{20}$ cycloaliphatic radical, or a $C_2$-$C_{20}$ aromatic radical.

Olefin monomers III are illustrated by 9,9-dioctyl-2-vinylfluorene; 9,9-dinonyl-2-vinylfluorene; 9,9-heptyl-2-vinylfluorene; 9,9-dimethyl-2-vinylfluorene; 9,9-dioctyl-3-vinylfluorene; 9,9-dioctyl-4-vinylfluorene; 9,9-dioctyl-2-acryloylfluorene; 9,9-dioctyl-2-methacryloylfluorene; 9,9-dioctyl-2-(1-trifluoromethylvin-1-yl)fluorene; 9,9-dioctyl-2-(1-fluorovin-1-yl)fluorene; 9,9-dioctyl-2-(1-chorovin-1-yl)fluorene; and the like.

Olefin monomers IV are illustrated by 9-vinylanthracene, 9-acryloylanthracene; 9-methacryloylanthracene; 9-anthracenylmethylmethacrylate (See Example 8 herein); and the like.

Olefin monomers V are illustrated by 1-vinylanthracene, 1-acryloylanthracene; 1-methacryloylanthracene; 1-anthracenylmethylmethacrylate; 2-vinylanthracene, 2-acryloylanthracene; 2-methacryloylanthracene; 2-anthracenylmethylmethacrylate (See Example 8 herein); and the like.

Olefin monomers VI are illustrated by 1-vinylnaphthalene; 1-acryloylnathalene; 1-methacryloylnathalene; 1-acryloyloxynathalene; 1-methacryloyloxynathalene; 2-vinylnaphthalene; 2-acryloylnathalene; 2-methacryloylnathalene; 2-acryloyloxynathalene; 2-methacryloyloxynathalene; 2-(1-trifluoromethylvin-1-yl)naphthalene; 2-(1-fluorovin-1-yl)naphthalene; and the like.

Heterocyclic olefin monomers are olefin monomers comprising at least one heterocyclic ring structure and are illustrated by heterocyclic olefin monomers VII, VIII, IX, and X

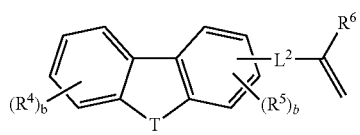

VII

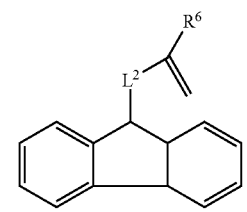

VIII wherein T is —O—, —S—, —Se—, —SS—, —SeSe—, —SO—, —SO$_2$—, —NH—, —NHNH—, a divalent $C_1$-$C_{20}$ aliphatic radical comprising at least one heteroatom, a divalent $C_3$-$C_{20}$ cycloaliphatic radical comprising at least one heteroatom, or a divalent $C_2$-$C_{20}$ aromatic radical comprising at least one heteroatom; $R^4$ and $R^5$ are independently at each occurrence hydrogen, a $C_1$-$C_{20}$ aliphatic radical, a $C_3$-$C_{20}$ cycloaliphatic radical, or a $C_2$-$C_{20}$ aromatic radical; "b" is independently at each occurrence 0, 1, 2, 3, or 4; "c" is a number from 0 to about 10; $L^2$ is a bond, a $C_1$-$C_{20}$ aliphatic radical, a $C_3$-$C_{20}$ cycloaliphatic radical, or a $C_2$-$C_{20}$ aromatic radical; and $R^6$ is hydrogen, halogen, a $C_1$-$C_{20}$ aliphatic radical, a $C_3$-$C_{20}$ cycloaliphatic radical, or a $C_2$-$C_{20}$ aromatic radical.

Heterocyclic olefin monomers VII are illustrated by 1-vinyldibenzofuran (T is oxygen); 1-vinyldibenzothiophene (T is sulfur); 1-vinyldibenzoselenophene (T is selenium); 2-vinyldibenzofuran; 2-vinyldibenzothiophene; 2-vinyldibenzoselenophene; 3-vinyldibenzofuran; 3-vinyldibenzothiophene; 3-vinyldibenzoselenophene; 4-vinyldibenzofuran; 4-vinyldibenzothiophene; 4-vinyldibenzoselenophene; 2-acryloyldibenzofuran; 2-acryloyldibenzothiophene; 2-acryloyldibenzoselenophene; 2-methacryloyldibenzofuran; 2-methacryloyldibenzothiophene; 2-methacryloyldibenzoselenophene; 3-vinyl-2,8-dioctyldibenzofuran; 4-vinyl-2,8-dimethyldibenzofuran; 3-vinyl-2,8-dioctyldibenzothiophene; 2-vinyl-2,8-dioctyldibenzoselenophene; and the like.

Heterocyclic olefin monomers VIII are illustrated by N-vinylcarbazole, N-allyl carbazole, N-(1-buten-4-yl)carbazole, N-acryloylcarbazole, N-methacryloylcarbazole; and the like.

Heterocyclic olefin monomers IX are illustrated by 2-vinylthiophene ("c"=0); 3,4-dimethyl-2-vinylthiophene; 5-vinyl-2,2'-dithiophene; 2-vinyl-3,4-dimethylthiophene trimer (See Example 20 herein); 2-vinyl-3,4-dimethylthiophene dimer; 2-vinyl-3-methyl-4-cyclohexylthiophene dimer (See Example 26 herein); and the like.

Heterocyclic olefin monomers X are illustrated by are illustrated by 2-vinylselenophene ("c"=0); 3,4-dimethyl-2-vinylselenophene; 5-vinyl-2,2'-diselenophene; 2-vinyl-3,4-dimethylselenophene trimer; 2-vinyl-3,4-dimethylselenophene dimer; 2-vinyl-3-methyl-4-cyclohexylselenophene dimer; and the like.

As noted, in one embodiment, "n" in structure II is independently at each occurrence an integer from 1 to about 200. As a result, heterocyclic compound I may be of relatively low molecular weight when the value of "n" is about 1, but because the $R^3$ group is repeated 4 times within structure I, the molecular weight of the heterocyclic compound I increases rapidly with an increasing value of "n". In one embodiment, each $R^3$ group is characterized a distinct and different value of "n". It is convenient moreover, to regard compositions having structure I as being characterized by an average value of "n", the average value of "n" being (when "m" is 1) the sum of the values of "n" for each of the four $R^3$ groups divided by 4. It will be appreciated by those skilled in the art that other methods of determining the average value of "n" are also available. For example, in the case of Example 7 herein, the average value of "n" was found to be about 3.2 by determining the number average molecular weight of compound I by gel permeation chromatography, determining (by difference) what portion of the number average molecular weight in grams per mole was attributable to structural units derived from 9,9-dioctyl-2-vinylfluorene, dividing that value by the molecular weight of 9,9-dioctyl-2-vinylfluorene, to determine the total number of structural units derived from 9,9-dioctyl-2-vinylfluorene, and dividing that value by eight. There is no requirement that the average value of "n" be an integer. For example, in one embodiment, the average value of "n" is a non-integer value such as 3.2 (See Example 7 herein).

In one embodiment, "n" independently at each occurrence has a value in a range from about 1 to about 50. In an alternate embodiment, "n" independently at each occurrence has a value in a in a range from about 1 to about 25. In yet another embodiment, "n" independently at each occurrence has a value in a in a range from about 1 to about 10.

The group Q is independently at each occurrence a hydrogen, a halogen, a $C_1$-$C_{20}$ aliphatic radical, a $C_3$-$C_{20}$ cycloaliphatic radical, or a $C_2$-$C_{20}$ aromatic radical. In one embodiment, the group Q represents a moiety which is susceptible to "group transfer" reaction. That is, Q in the presence of an initiator may participate in a group transfer reaction or group transfer polymerization. Examples 7 and 8 of the instant application are illustrative of group transfer reactions in which the group transferred, Q, is a bromine atom (atom transfer) In the Examples 7 and 8 just referred to, an initiator, cuprous bromide (CuBr), is employed in order to effect the group transfer polymerization. Thus, in one embodiment of the present invention, Q is a bromine atom. Group transfer reactions involving the transfer of a single atom are sometimes referred to as "atom transfer" reactions. In an alternate embodiment, Q is an organic moiety susceptible to group transfer reaction. Thus, in one embodiment, Q is a moiety having structure XVI. The foregoing discussion should not be read, however, to limit Q to groups susceptible to participation in a group transfer reaction or group transfer polymerization.

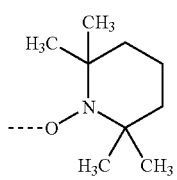

XVI

As noted, "m" is independently at each occurrence an integer from 1 to about 10. In one embodiment, the value of "m" is determined by the number and reactivity of functional groups present in an aromatic aldehyde used in the preparation of the porphyrin precursor. Thus, for example, condensation of pyrrole with 3,5-dihydroxybenzaldehyde affords a porphyrin precursor having 8 reactive hydroxyl groups which may be used to elaborate the compositions of the present invention. Under such circumstances, the moiety $Ar^1$ will have structure XII and "m" will have a value of 2. Those skilled in the art will understand that the higher values of "m" are achievable. In one embodiment, a heterocyclic precursor porphyrin having 12 reactive hydroxyl groups which may be used to elaborate the compositions of the present invention, is prepared by reacting an aromatic aldehyde having three hydroxy groups with pyrrole. Synthetic methods for the preparation of such precursor porphyrins are well known in the art. See for example, The Porphyrin Handbook, Karl Kadish, Kevin Smith and Roger Guilard Ed.s (Academic Press, 1999).

In one embodiment, the present invention provides a composition comprising heterocyclic structure I, wherein "a" is 0; M is selected from the group consisiting of $Pd^{2+}$ and $Pt^{2+}$; $R^1$ and $R^2$ are H; $Ar^1$ is an aromatic radical selected from the group consisting of divalent aromatic radicals XI and XII;

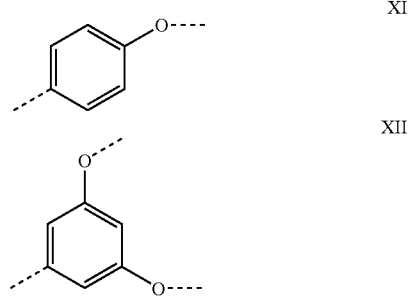

$L^1$ is a divalent aliphatic radical having structure XIII;

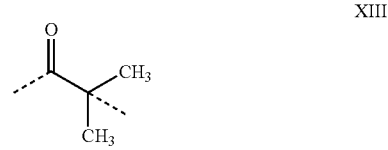

F is an olefin monomer-derived moiety having structure XIV

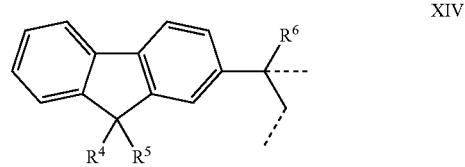

wherein $R^4$ and $R^5$ are independently at each occurrence hydrogen, a $C_1$-$C_{20}$ aliphatic radical, a $C_3$-$C_{20}$ cycloaliphatic radical, or a $C_2$-$C_{20}$ aromatic radical, and $R^6$ is independently at each occurrence a halogen, a $C_1$-$C_{20}$ aliphatic radical, a $C_3$-$C_{20}$ cycloaliphatic radical, or a $C_2$-$C_{20}$ aromatic radical;

"n" is independently at each occurrence an integer from 2 to about 10; Q is Br; and "m" is 1 or 2.

In an alternate embodiment, the present invention provides a composition comprising heterocyclic structure I, wherein "a" is 0; M is selected from the group consisiting of $Pd^{2+}$ and $Pt^{2+}$; $R^1$ and $R^2$ are H; $Ar^1$ is an aromatic radical selected from the group consisting of divalent aromatic radicals XI and XII;

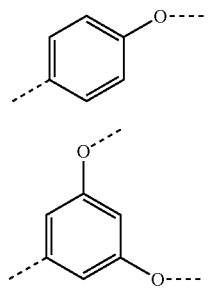

XI

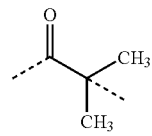

XII $L^1$ is a divalent aliphatic radical having structure XIII;

XIII

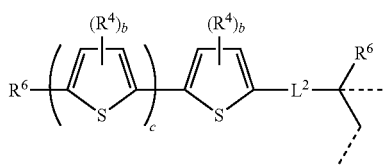

F is an olefin monomer-derived moiety having structure XV

XV

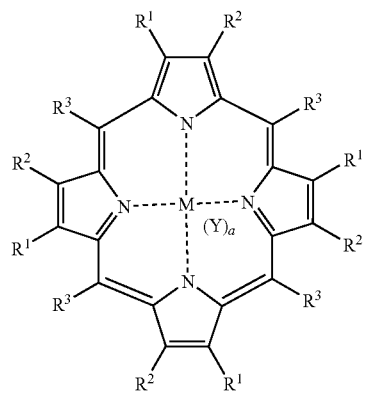

wherein $R^4$ is independently at each occurrence hydrogen, a $C_1$-$C_{20}$ aliphatic radical, a $C_3$-$C_{20}$ cycloaliphatic radical, or a $C_2$-$C_{20}$ aromatic radical, and $R^6$ is independently at each occurrence a halogen, a $C_1$-$C_{20}$ aliphatic radical, a $C_3$-$C_{20}$ cycloaliphatic radical, or a $C_2$-$C_{20}$ aromatic radical;

"b" is independently at each occurrence 0, 1, or 2; "c" is a number from 0 to about 10; "n" is independently at each occurrence an integer from 2 to about 10; Q is Br; and "m" is 1 or 2.

The compositions of the present invention include compositions having, in one embodiment, a number average molecular weight in a range from about 1000 grams per mole to about 500,000 grams per mole. In an alternate embodiment, the composition of the present invention has a number average molecular weight in a range from about 1000 grams per mole to about 25,000 grams per mole. In yet another embodiment, the composition of the present invention has a number average molecular weight in a range from about 2000 grams per mole to about 10,000 grams per mole. Number average molecular weights may be determined by a variety of methods, for example by proton NMR or gel permeation chromatography. The molecular weight ranges given here are determined by gel permeation chromatography.

In one embodiment, the present invention provides an organic phosphor comprising heterocyclic structure I. In an alternate embodiment, the present invention provides an organic phosphor comprising heterocyclic structure I, said organic phosphor exhibiting a red phosphorescence when irradiated.

In one embodiment, the present invention provides an organic phosphor having structure I wherein "a" is 0, and M is selected from the group consisting of $Pd^{2+}$ and $Pt^{2+}$. In an alternate embodiment, the present invention provides an organic phosphor having structure I wherein "a" is 0, and M is $Pt^{2+}$. In yet another embodiment, the present invention provides an organic phosphor having structure I wherein "a" is 0, and M is $Pd^{2+}$.

In yet another aspect, the present invention provides a method for the preparation of a composition comprising heterocyclic structure I. The method comprises contacting in the presence of an initiatior a heterocyclic precursor compound having structure XVII

XVII wherein M is a divalent, trivalent or tetravalent metal; "a" is 0, 1, 2, or a non-zero fraction having a value between 0 and 1; Y is independently at each occurrence a charge balancing counterion; $R^1$ and $R^2$ are independently at each occurrence a halogen, a $C_1$-$C_{20}$ aliphatic radical, a $C_3$-$C_{20}$ cycloaliphatic radical, a $C_2$-$C_{20}$ aromatic radical, or $R^1$ and $R^2$ may together form a divalent aliphatic radical, a divalent cycloaliphatic radical, or a divalent aromatic radical; $R^3$ is independently at each occurrence an organic radical having structure XVIII

XVIII

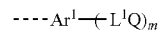

wherein $Ar^1$ is a $C_2$-$C_{50}$ aromatic radical; $L^1$ is a $C_1$-$C_{20}$ aliphatic radical, a $C_3$-$C_{20}$ cycloaliphatic radical, or a $C_2$-$C_{20}$ aromatic radical; Q is a halogen susceptible to group transfer, a $C_1$-$C_{20}$ aliphatic radical susceptible to group transfer, a $C_3$-$C_{20}$ cycloaliphatic radical susceptible to group transfer, or a $C_2$-$C_{20}$ aromatic radical susceptible to group transfer; and "m" is an integer from 1 to about 10;

with at least one olefin monomer selected from the group consisting of polycyclic olefin monomers and heterocyclic olefin monomers.

As used herein, the term "susceptible to group transfer" means that the moiety being described can be induced to participate in a group transfer reaction or group transfer polymerization. For the purposes of this disclosure, the terms "group transfer reaction" and "group transfer polymerization" are defined to include "atom transfer reaction" and "atom transfer polymerization". For example, the reaction described in Example 7 of the instant invention represents a group transfer reaction in which the "group" transferred is a bromine atom.

EXAMPLES

The following examples are intended only to illustrate methods and embodiments in accordance with the invention, and as such should not be construed as imposing limitations upon the claims.

Preparation of Porphyrin Intermediates

Example 1

Preparation of 5,10,15,20-tetrakis(3',5'-di(hydroxy)phenyl)porphyrin palladium(II) XIX: A 50 mL serum vial containing 30 mL of benzonitrile was charged with palladium(II) acetylacetonate (0.475 g, 1.56 mmoles, Strem Chemicals, Newburyport, Mass., USA) and 5,10,15,20-tetrakis(3',5'-di(hydroxy)phenyl)-21H-23H-porphyrin (1.0 g, 1.3 mmoles, TCI Chemicals, Tokyo, Japan). The solution was sealed with a crimp cap and degassed under bubbling nitrogen for 30 minutes. The degassed solution was then heated to 190° C. in an aluminum block with stirring for 23 hours. The solution was allowed to cool to ambient temperature before slow precipitation into 100 mL chloroform to afford palladium complex XIX (wherein, making reference to structure I: $M=Pd^{2+}$, "a"=0, $R^1=R^2=H$, $R^3=Ar^1(L^1(F)_nQ)_m$ wherein "m" is 0 and $Ar^1$ is 3,5-dihydroxyphenyl) as a bright red precipitate which was collected by vacuum filtration and dried in vacuo (65° C., 18 hours, 1.1 g, 1.29 mmoles, 99%). $^1$H-NMR ($d_6$-DMSO) δ 6.64 (4H, t), 6.98 (8H, d), 8.89 (8H, s).

Example 2

Preparation of heterocyclic precursor compound XX, 5,10,15,20-tetrakis(3',5'-bis(2-bromo-2-methylpropionyloxy)phenyl)porphyrin palladium(II): To a solution of 5,10,15,20-tetrakis(3',5'-di(hydroxy)phenyl)porphyrin palladium(II) XIX (1.1 g, 1.29 mmoles) in pyridine (20 mL) was added α-bromoisobutyryl bromide (5.0 g, 21.7 mmoles, Aldrich, Milwaukee, Wis., USA). After the initial exotherm, pyridinium hydrobromide precipitated. Once the deep red mixture was cooled to ambient temperature, 10 mL of distilled water was added to quench unreacted α-bromoisobutyryl bromide. The mixture was filtered to remove the pyrdinium hydrobromide salt. Pyridine was removed by rotary evaporation leaving a dark red oil. The dark red oil was dissolved in a minimum amount of methylene chloride and precipitated into methanol to afford the product octaester XX (wherein, making reference to structure I: $M=Pd^{2+}$, "a"=0, $R^1=R^2=H$, $R^3=Ar^1(L^1(F)_nQ)_m$ wherein $Ar^1$ has structure XII, $L^1$ has structure XIII, Q is Br, "n" is 0, and "m" is 2) as a dark red solid (2.19 g, 1.07 mmoles, 83%). $^{13}$C-NMR (CDCl$_3$) δ 30.62, 55.03, 114.39, 119.63, 124.77, 131.55, 141.39, 143.47, 149.52, 170.03.

Example 3

Preparation of 5,10,15,20-tetrakis(4'-hydroxyphenyl)porphyrin palladium(II) XXI: To 15 mL of stirred benzonitrile in a 20 mL serum vial was charged palladium(II) acetylacetonate (0.370 g, 1.21 mmoles, Strem Chemicals, Newburyport, Mass., USA) and 5,10,15,20-tetrakis(4'-hydroxyphenyl)-21H-23H-porphyrin (0.75 g, 1.1 mmoles, Aldrich Chemical, Milwaukee, Wis., USA). The vial was sealed with a crimp cap and degassed with nitrogen for 30 minutes. The degassed solution was then stirred and heated at 190° C. in an aluminum block for 23 hours. The solution containing the product was allowed to cool to ambient temperature before slow precipitation into 50 mL chloroform. The bright red precipitate was collected by vacuum filtration and dried in vacuo (65° C., 10 hours) to give the product XXI (wherein, making reference to structure I: $M=Pd^{2+}$, "a"=0, $R^1=R^2=H$, $R^3=Ar^1(L^1(F)_nQ)_m$ wherein "m" is 0 and $Ar^1$ is 4-hydroxyphenyl) (0.78 g, 1.0 mmoles, 99%). $^1$H-NMR ($d_6$-DMSO) δ 7.20 (8H, d), 7.95 (8H, d), 8.85 (8H, s), 9.96 (4H, s).

Example 4

Preparation of heterocyclic precursor compound XXII, 5,10,15,20-tetrakis(4'-(2-bromo-2-methylpropionyloxy)phenyl)porphyrin palladium(II): To a solution of 5,10,15,20-tetrakis(3',5'-di(hydroxy)phenyl)porphyrin palladium(II) (0.35 g, 0.44 mmoles) in pyridine (5 mL) was added 2-bromoisobutyryl bromide (0.93 g, 4.0 mmoles). After the initial exotherm, pyridinium hydrobromide was observed to precipitate. The deep red mixture was cooled to ambient temperature, and 2 mL of distilled water was added to quench unreacted 2-bromoisobutyryl bromide. The resultant mixture was filtered and the filtrate was concentrated by rotary evaporation to give a dark red oil. The dark red oil was dissolved in a minimum amount of methylene chloride and precipitated into methanol to afford upon filtration the product tetraester XXII (wherein, making reference to structure I: $M=Pd^{2+}$, "a"=0, $R^1=R^2=H$, $R^3=Ar^1(L^1(F)_nQ)_m$ wherein $Ar^1$ has structure XI, $L^1$ has structure XIII, Q is Br, "n" is 0, and "m" is 1) as a dark red solid (2.19 g, 1.07 mmoles, 83%). $^1$H-NMR (CDCl$_3$) δ 2.26 (24H, s), 7.59 (8H, d), 8.23 (8H, d), 8.87 (8H, s).

Example 5

Preparation of palladium heterocycle XXIII: To 5 mL of stirred benzonitrile in a 20 mL serum vial was charged palladium(II) acetylacetonate (15 mg, 0.05 mmoles, Strem Chemicals, Newburyport, Mass., USA) and 5,10,15,20-tetrakis(3',5'-bis(2-phenyl-2-(2',2',6',6'-tetramethyl-1-piperidinyloxy)ethoxycarbonyl)phenyl)porphyrin (100 mg, 0.03 mmoles, Frontier Scientific, Logan, Utah, USA). The vial was sealed with a crimp cap and degassed with nitrogen for 15 minutes. The degassed solution was then stirred and heated at 150° C. in an aluminum block with stirring for 15 hours. The solution was allowed to cool to ambient temperature before slow precipitation into 50 mL hexanes. The collected dark orange solid was redissolved in 1 mL THF and re-precipitated in hexanes to afford a bright orange precipitate which was collected by vacuum filtration and dried in vacuo (65° C., 18 hours) to afford the product palladium heterocycle 5,10,15,20-tetrakis(3',5'-bis(2-phenyl-2-(2',2',6',6'-tetramethyl-1-piperidinyloxy)ethoxycarbonyl)phenyl)porphyrin palladium (II) XXIII (wherein, making reference to structure I: $M=Pd^{2+}$, "a"=0, $R^1=R^2=H$, $R^3=Ar^1(L^1(F)_nQ)_m$ wherein $Ar^1$ is the trivalent aromatic radical 3,5-dicarbonyl-phen-1-yl, $L^1$ is the divalent aromatic radical —OCH$_2$CH(Ph)-, Q is a $C_9$ cycloaliphatic radical having structure XVI, "n" is 0, and "m" is 2) ((49 mg, 0.015 mmoles, 47%). $^1$H-NMR (CDCl$_3$) δ 8.81 (8H, s), 8.30 (12H, m), 7.52 (40H, br m), 5.25 (8H, m, ABX), 5.05 (8H, m, ABX), 4.79 (8H, m, ABX), 1.75-1.18 (96H, m), 1.15 (24H, s) 0.85 (24H, s).

Example 6

Preparation of palladium heterocycle XXIV: A 20 mL serum vial containing 5 mL of benzonitrile was charged with palladium(II) acetylacetonate (39 mg, 0.05 mmoles) and 5,10,15,20-tetrakis(4'-(2-phenyl-2-(2',2',6',6'-tetramethyl-1-piperidinyloxy)ethoxycarbonyl)phenyl)porphyrin (200 mg, 0.11 mmoles, Frontier Scientific, Logan, Utah, USA). The vial was sealed with a crimp cap and degassed with nitrogen for 15 minutes. The degassed solution was then stirred and heated at 150° C. in an aluminum block for 15 hours. The solution was allowed to cool to ambient temperature before slow precipitation into 50 mL of hexanes. The collected dark orange solid was then redissolved in 1 mL THF and re-precipitated in hexanes to afford a bright orange precipitate which was collected by vacuum filtration and dried in vacuo (65° C., 18 hours). The product palladium heterocycle XXIV (196 mg, 1.29 mmoles, 93%) 5,10,15,20-tetrakis(4'-(2-phenyl-2-(2',2',6',6'-tetramethyl-1-piperidinyloxy)ethoxycarbonyl)phenyl)porphyrin palladium (II) (wherein, making reference to structure I: M=Pd, "a"=0, $R^1=R^2=H$, $R^3=Ar^1(L^1(F)_n Q)_m$ wherein $Ar^1$ is the divalent aromatic radical 4-carbonyl-phen-1-yl, $L^1$ is the divalent aromatic radical —OCH$_2$CH(Ph)-, Q is a $C_9$ cycloaliphatic radical having structure XVI, "n" is 0, and "m" is 1) was characterized by proton NMR. $^1$H-NMR (CDCl$_3$) δ 8.85 (8H, s), 8.30 (16H, d), 7.48 (20H, m), 5.22 (4H, t, ABX), 5.00 (4H, dd, ABX), 4.77 (4H, dd, ABX), 1.72-1.20 (48H, m), 1.15 (12H, s) 0.85 (12H, s).

The structures of intermediates XIX-XXIV discussed in Examples 1-6 are gathered in Table 2.

TABLE 2

INTERMEDIATES

| Entry* | $Ar^1$ | $R^3$ | | | | |
| | | $L^1$ | F | Q | n | m |
|---|---|---|---|---|---|---|
| XIX | 3,5-dihydroxyphenyl | — | — | — | — | 0 |
| XX | 3,5-bis(isobutyryloxy)phenyl | isobutyryloxy linker | — | Br | 0 | 2 |
| XXI | 4-hydroxyphenyl | — | — | — | — | 0 |
| XXII | 4-(isobutyryloxy)phenyl | isobutyryloxy linker | — | Br | 0 | 1 |
| XXIII | 3,5-dicarbonylphenyl | —OCH(Ph)CH$_2$— | — | 2,2,6,6-tetramethyl-1-piperidinyloxy | 0 | 2 |
| XXIV | 4-carbonylphenyl | —OCH(Ph)CH$_2$— | — | 2,2,6,6-tetramethyl-1-piperidinyloxy | 0 | 1 |

*Structures are referenced to heterocycle I wherein M = Pd$^{2+}$, "a" = 0, $R^1 = R^2 = H$, and $R^3 = Ar^1(L^1(F)_n Q)_m$ Group/Atom Transfer Polymerization Example 7

Polymer XXV: A 20 mL serum vial containing 5 mL solution of anisole was charged with the heterocyclic precursor compound XX (25 mg, 0.05 mmoles) prepared in Example 2, 2-vinyl-9,9-dioctylfluorene (1.01 g, mmoles, See Example 12 below), copper(I) bromide (28 mg, mmoles), and pentamethylenediethyltriamine (33.7 mg). The vial was sealed with a crimp cap and degassed with nitrogen for 15 minutes. The degassed solution was then stirred and heated at 90° C. in an aluminum block for 1 hour whereupon the viscosity of the reaction solution was observed to be appreciably higher as evidenced by persistence of bubbles at the upper meniscus of the solution. The solution was allowed to cool to ambient temperature before slow precipitation into 40 mL methanol. A pink fluffy solid was collected by vacuum filtration and redissolved in 1 mL methylene chloride and re-precipitated in methanol to afford a fluffy light solid which was collected by vacuum filtration and dried in vacuo (65° C., 4 hours) to afford the product polymer (156 mg) having structure XXV (wherein, making reference to structure I: $M=Pd^{2+}$, "a"=0, $R^1=R^2=H$, $R^3=Ar^1(L^1(F)_nQ)_m$ wherein $Ar^1$ has structure XII, $L^1$ has structure XIII, Q is Br, "n" has an average value of about 3.2, and "m" is 2). The molecular weight of the product polymer was determined by gel permeation chromatography (GPC) and molecular weights are referenced to polystyrene (PS) molecular weight standards. $M_w=14338$ grams per mole, $Mn=12884$ grams per mole. The average value of "n" was determined to be about 3.2 based upon the number average molecular weight (12884 grams per mole). The UV-Vis (chloroform) spectrum exhibited absorption maxima at 275, 296, 308, 417, 523, 599 nanomers. Solid state excitation of the product polymer with a UV lamp revealed a robust, red phosporesent emission.

Example 8

Polymer XXVI: To a 20 mL serum vial containing 4 mL dry toluene was charged palladium porphyrin prepared in Example 2 (50 mg, 0.1 mmoles), 2-vinyl-9,9-dioctylfluorene (0.4 g, 0.96mmoles, See Example 12 below), and 9-anthracenylmethyl methacrylate (0.312 grams 1.1 mmoles), copper (I) bromide (54 mg), and pentamethylenediethyltriamine (70 mg, mmoles). The vial was sealed with a crimp cap and degassed with nitrogen for 15 minutes. The degassed solution was then stirred and heated at 90° C. in an aluminum block for 30 minutes after which time the product mixture had a honey-like viscosiy. The viscous product solution was allowed to cool to ambient temperature before slow precipitation into 40 mL methanol. A pink fluffy solid was collected by vacuum filtration and re-dissolved in 4 mL methylene chloride and re-precipitated in methanol to afford a fluffy light solid which was collected by vacuum filtration and dried in vacuo (65° C., 4 hours) to provide the product polymer XXVI (432 mg). GPC (PS reference) $M_w=26516$ grams per mole, $M_n=22998$ grams per mole, PDI=1.15, UV-Vis (chloroform) 275, 296, 308, 331, 348, 366, 387, 415.

The structures of product polymers XXV-XXVI discussed in Examples 7-8 are gathered in Table 3.

TABLE 3

PRODUCT POLYMERS

| Entry* | $Ar^1$ | $L^1$ | F (R³) | Q | $n^a$ | m |
|---|---|---|---|---|---|---|
| XXV | (3-substituted phenoxy) | isobutyryl ester | 9,9-dioctylfluorene | Br | 3.2 | 2 |
| XXVI | (3-substituted phenoxy) | isobutyryl ester | 9,9-dioctylfluorene with 9-anthracenylmethyl methacrylate | Br | 8 | 2 |

*Structures are referenced to heterocycle I wherein $M = Pd^{2+}$, "a" = 0, $R^1 = R^2 = H$, and $R^3 = Ar^1(L^1(F)_nQ)_m$.
$^a$average value of "n".

Polycyclic and Heterocyclic Olefin Monomers

Example 9

Preparation of 2-bromo-9,9-dioctylfluorene: A mixture of 2-bromofluorene (100 g, 0.4 mol), in DMSO (320 ml), Bu₄NBr (8.0 g, 25 mmol) and NaOH (50%, 160 mL) was degassed with argon for 30 min. To the resultant solution was added 1-bromooctane (d=1.18 g/mol, 232 mL). The mixture was stirred under Ar at 60 °C. for an hour, until HPLC indicated complete conversion of the 2-bromofluorene to product. The reaction mixture was then cooled, 600 mL of ether and 400 mL of water were added, and the mixture was transferred to a separatory funnel. The aqueous phase was extracted with ether (2×300 mL), the combined ether layer was washed with 10% HCl (2×), water (3×) and brine (1×). Removal of solvent in vacuo afforded 320 g of an oil. Excess 1-bromooctane (99.12 g) was removed by vacuum distillation (120 °C. for 2 hours, and 150 °C. for 2 hours at 1 torr). The pot residue (~163.4 g) was shown by $^1$H NMR the product 2-bromo-9,9-dioctylfluorene (85.3% yield). EI-MS: 470 (M+2), 468 (M+). $^1$H NMR (CDCl$_3$) δ 7.4-7.8 (m, 7H), 2.0 (dd, CH$_2$, 4H), 1.2 (m, CH$_2$, 22H), 0.85 (t, 5H), 0.6 (t, CH$_3$, 3H). $^{13}$C NMR (CDCl$_3$) δ 152.98, 150.32, 140.14, 140.03, 129.85, 127.45, 126.90, 126.14, 124.40, 122.88, 121.02, 119.73, 55.37, 47.52, 40.28, 31.75, 29.94, 29.19, 23.68, 22.62, 14.17.

Example 10

Preparation of 2-formyl-9,9-dioctylfluorene: To a dry 500 mL flask equipped with an argon inlet, a rubber septum, and a distillation head was charged 22.54 g (48.0 mmol) of 9,9-dioctyl-2-bromofluorene and 100 mL of toluene. Toluene was then removed by distillation to dry the flask and starting material. The residue was allowed to cool to room temperature and 250 mL of anhydrous ether was added. The resultant solution was then chilled to −78 °C. and treated dropwise over 15 minutes with 30.6 mL (49.06 mmol) of 1.6M BuLi in hexane. Upon addition of the butyl lithium solution the reaction mixture initially turned purple and subsequently turned red. Anhydrous DMF (8 mL) was added and the resulting mixture was stirred at −78 °C. for 1 hour and then warmed up to room and stirred for an additional hour. The mixture was quenched with 50 mL of 10% HCl and transferred into a separatory funnel. The organic phase was washed with 10% HCl (1×), water (2×) and brine (1×), and then dried over MgSO$_4$. Solvent removal afforded 12 g of crude product. Purification by column chromatography (gradient from 96:4 heptanes: EtOAc in heptanes to 90:10 heptanes:EtOAc) afforded 10.2 g of 2-formyl-9,9-dimethylfluorene (49.77% yield). EI-MS: 418 (M+), 362,193 (100). $^1$H NMR (CDCl$_3$) δ 10.09 (s, 1H), 7.87 (m, 4H), 7.41 (b, 3H), 2.05 (m, 4H), 1.30-1.05 (m, 22H), 0.83 (t, 5H), 0.61 (t, 3H). $^{13}$C NMR (CDCl$_3$) δ 192.22, 152.11, 151.55, 147.54, 139.53, 135.39, 130.40, 128.78, 127.10, 123.09, 120.98, 120.91, 119.93, 70.98, 55.32, 40.24, 31.88, 29.92, 29.17, 23.78, 22.59, 14.03.

Exanple 11

Preparation of 2-vinyl-9,9-dioctylfluorene: To a solution of methyltriphenylphosphonium bromide (714 mg, 2 mmol) in ether at 0° C. was added dropwise 1.6 M n-BuLi solution in hexane (1.25 mL, 2.00 mmol). The solution was stirred at 0° C. for 40 min and then was warmed to room temperature. A solution of 2-formyl-9,9-dioctylfluorene (585 mg, 1.4 mmol) was then added and reaction mixture was stirred overnight. The reaction mixture was quenched with 20 mL of 1% HCl. The mixture was extracted with ether and the organic layer was washed with NaHCO$_3$ solution, and brine solution, and dried over MgSO$_4$. The solvent was removed in vacuo and the product was purified by column chromatography on silica gel using hexane as the elutant to afford the purified 2-vinyl-9,9-dioctylfluorene (0.2834 g, 49% yield). EI-MS: 416 (M+), 360,192 (100). $^1$H NMR (CDCl$_3$) δ 7.66 (m, 2H), 7.42-7.32 (m, 5H), 6.83 (dd, 1H), 5.82 (d, 1H), 5.28 (d, 1H), 1.97 (m, 4H), 1.28-1.06 (m, 22H), 0.83 (t, 5H), 0.63 (t, 3H). $^{13}$C NMR (CDCl$_3$) δ151.09, 151.00, 141.08, 140.8, 137.51, 136.47, 127.05, 126.77, 125.21, 122.88, 120.54, 119.69 (2C), 112.89, 54.97, 40.39, 31.84, 31.65, 30.09, 29.25, 23.75, 22.65, 14.10

Example 12

Preparation of 3,4-dimethylthiophene: A pre-heated 4 L 3-neck round bottom flask fitted with a reflux condenser and pressure equalizing addition funnel was purged with nitrogen until cool. The flask was then charged with 1,3-bis(diphenylphosphino)propane (dppp) NiCl$_2$ (5.0 grams, mmoles) and suspended in 300 mL dry ether. Then, 3,4-dibromothiophene (200 grams, mmoles) was added via canula. The pressure equalizing addition funnel was charged with 3.0 M methyl magnesium bromide (800 mL) which was added dropwise over the course of 3 hours. The color of the reaction mixture darkened from bright red initially to a dark orange-brown color. The reaction mixture was heated at reflux for 48 hours. Upon cooling, 1.0 liter (L) of 1N hydrochloric acid was added to the vigorously stirred mixture. The phases were separated and the aqueous phase was extracted with ether (3×500 mL). The organic phase and extracts were combined, washed with brine (1×1.0 L), and dried over sodium sulfate. The volatiles were removed in vacuo leaving a dark brown oil (85 grams). Distillation of the oil at 58° C. at 40 mm Hg yielded the product 3,4-dimethylthiophene as a colorless oil (73.2 g). $^1$H-NMR (benzene-d$_6$) δ 6.71 (2H, s), 1.99 (6H, s).

Example 13

Preparation of 2-bromo-3,4-dimethylthiophene: A solution of N-bromosuccinimide (NBS) (41.85 g, 0.24 mol) in 150 mL of DMF was added dropwise into a flask containing 3,4-dimethylthiophene (30.0 g, 0.267 mol) in dimethylformamide (DMF) (300 mL) at 0° C. over a period of 1 h. After the addition, the cooling bath was removed and the resulting mixture was stirred for 2 h at room temperature. The mixture was quenched with ice-water (300 mL) and extracted with ether (50 mL) three times. The combined organic extracts were washed with water, and dried over MgSO$_4$. Solvent removal followed by fractional vacuum distillation yielded the product 2-bromo-3,4-dimethylthiophene as a pale yellow liquid (35.0 g, 70%). $^1$H NMR (CDCl$_3$) δ 6.88 (1H, s), 2.20 (3H, s), 2.12 (3H, s).

Example 14

Preparation of 2,5-dibromo-3,4-dimethylthiophene: To a solution of 3,4-dimethylthiophene (15.0 g, 0.133 mol) in DMF (100 mL) was added a solution of NBS (54 g, 0.85 mol) in DMF (150 mL) dropwise at room temperature. After the addition, the reaction mixture was stirred at room temperature for 2 h. The mixture was poured into ice water and extracted with either (50 mL) three times. The combined organic extracts were washed with water (three times) and dried over MgSO$_4$. Removal of the solvent afforded the product 2,5-dibromo-3,4-dimethylthiophene as a yellow liquid (35 g, 90%). $^1$H NMR (CDCl$_3$) δ 2.14 (6H, s, CH$_3$).

Example 15

Preparation of 3,4-dimethylthiophene dimer: To a reaction vessel containing dry THF (30 mL) was added magnesium turnings (0.60 g, 25 mmol) and 2-bromo-3,4-dimethylthiophene (3.5 g, 18.2 mmol) under nitrogen. The resultant mixture was refluxed for 3 h to afford a solution of the Grignard reagent 3,4-dimethylthienylmagnesium bromide. The solution containing the Grignard reagent was transferred to an additional funnel and added dropwise under nitrogen into a flask containing 2-bromo-3,4-dimethylthiophene (3.5 g, 18.2 mmol) and dppp $NiCl_2$ (60 mg) in dry THF (30 mL) at room temperature over a period of 30 min. Upon completion of the addition, the reaction mixture was heated overnight at reflux. The mixture was then quenched with a saturated solution of ammonium chloride and extracted with ether (3×50 mL). The combined organic phases were washed with water and brine, and dried over $MgSO_4$. Removal solvent and purification by chromatography (silica gel) afforded a crude product which was recrystallized from hexane to give 3,4-dimethylthiophene dimer as a white solid (2.41 g, 60%). $^1$H NMR ($CDCl_3$) δ 6.96 (2H, s, aromatic H), 2.22 (6H, s, $CH_3$), 2.05 (6H, s, $CH_3$).

Example 16

Preparation of 3,4-dimethylthiophene trimer: The preparation of the trimer followed a procedure analogous to that used in Example 15. The Grignard reagent prepared from 2-bromo-3,4-dimethylthiophene (14.3 g, 73 mmol) and magnesium turnings (2.4 g, 100 mmol) in dry THF (60 mL) was added dropwise under nitrogen into a flask containing 2,5-dibromo-3,4-dimethylthiophene (8.0 g, 29.4 mmol) and dppp $NiCl_2$ (450 mg) at room temperature. After the addition, the reaction mixture was heated overnight at reflux. The crude product was isolated as in Example 15. Recrystallization from a mixture of hexane and ethanol gave the product 3,4-dimethylthiophene trimer as a white solid (7.10 g, 73%). $^1$H NMR ($CDCl_3$) δ 7.01 (2H, s, aromatic H), 2.27 (6H, s, $CH_3$), 2.16 (12H, s, $CH_3$).

Example 17

Preparation of 2-formyl-3,4-dimethylthiophene dimer (2-formyl-5-(3',4'-dimethylthienyl)-3,4-dimethylthiophene): 3,4-dimethylthiophene dimer (2.42 g, 11 mmol) was dissolved in 10 mL DMF. A solution of DMF and $POCl_3$ (30 mL, 4:1 DMF:$POCl_3$) was added cautiously at 0° C. and the mixture was stirred overnight at room temperature. The reaction mixture was then poured into ice water, neutralized with 25% NaOH solution (to pH~8). The mixture was then extracted with dichloromethane. Evaporation of the dichloromethane gave the crude product which was purified by column chromatography on silica gel. Dichloromethane-petroleum ether (1:3) was used as the eluant. The product 2-formyl-5-(3',4'-dimethylthienyl)-3,4-dimethylthiophene (2.3 g, 85% yield) was characterized by NMR. 1H NMR (CDCl3) δ 10.07 (1H, s, CHO), 7.03 (1H, s, aromatic H), 2.53 (3H, s, CH3), 2.22 (3H, s, CH3), 2.10 (3H, s, CH3), 2.08 (3H, s, CH3).

Example 18

Preparation of 2-formyl-3,4-dimethylthiophene trimer (Method A): A solution of 1.5 M n-butyllithium (3.4 mL, 5.1 mmol) in ether was added dropwise under argon to a solution of 3,4-dimethylthiophene trimer (1.62 g, 4.8 mmol, See Example 16) in dry THF (10 mL) at −70° C. and the resultant solution was warmed to −50° C. Next, 0.4 mL (5.4 mmol) of DMF was added dropwise and the mixture allowed to warm to room temperature overnight. The mixture was poured into a mixture of 1 liter of 12 M HCl and crushed in certain embodiments and thereafter extracted with ether. The organic layers were combined, washed with water, and dried over $MgSO_4$. After evaporation of the solvent, the residue was purified by column chromatography (silica gel, hexane/$CH_2Cl_2$ (v:v) 3:1) to give the product 2-formyl-3,4-dimethylthiophene as a yellow solid (0.98 g, 56%) and recovered unreacted trimer (0.55 g). $^1$H NMR ($CDCl_3$) δ 10.08 (1H, s, CHO), 6.99 (1H, s, aromatic H), 2.53 (3H, s, $CH_3$), 2.22 (3H, s, $CH_3$), 2.16 (3H, s, $CH_3$), 2.13 (3H, s, $CH_3$), 2.10 (6H, s $CH_3$).

Example 19

Preparation of 2-formyl-3,4-dimethylthiophene trimer (Method B): To a solution of 3,4-dimethylthiophene trimer (3.7 g, 11 mmol) in 20 mL of a DMF: $CHCl_3$ (1:1, v:v) solvent mixture, was added 20 mL of a solution of DMF and $POCl_3$ (4:1, v:v). The DMF:$POCl_3$ mixture was added cautiously, dropwise at 0° C. Following the addition, the reaction mixture was allowed to warm to ambient temperature and was stirred overnight. The reaction mixture was then poured into ice water and neutralized with 25% NaOH solution to pH~8. The aqueous mixture was extracted with dichloromethane. Upon solvent removal the residue was subjected to purification by column chromatography using silica gel and a dichloromethane-petroleum ether (1:3) mixed solvent as the eluting solution to yield pure product 2-formyl-3,4-dimethylthiophen trimer 2.2 g (Yield: 55%) $^1$H NMR (CDCl3) δ 10.09 (1H, s, CHO), 7.00 (1H, s, aromatic H), 2.54 (3H, s, CH3), 2.23 (3H, s, CH3), 2.16 (3H, s, CH3), 2.13 (3H, s, CH3), 2.11 (6H, s, CH3), and the corresponding trimer dialdehyde 1.57 g (Yield: 37%) $^1$H NMR (CDCl3) δ 10.09 (2H, s, CHO), 2.54 (6H, s, CH3), 2.15 (12H, m, CH3).

Example 20

Preparation of 2-vinyl-3,4-dimethylthiophene trimer: To a solution of methyltriphenylphosphonium bromide (714 mg, 2 mmol) in ether at 0° C. was added dropwise 1.6 M n-BuLi solution in hexane (1.25 mL, 2.00 mmol). The resultant solution was stirred at 0° C. for 40 min and then was warmed to room temperature. A solution of 2-formyl-3,4-dimethylthiophene trimer (432 mg, 1.2 mol) was added slowly and the mixture was stirred overnight. The reaction mixture was quenched with ammonium chloride solution and diluted with ether. The organic phase was washed with water and brine, and dried with $MgSO_4$. The ether was removed in vacuo to afford the crude product as an oil (260 mg). Column chromatography (2% EtOAc in hexane) afforded the purified 2-vinyl-3,4-dimethylthiophene trimer (140 mg, 37% yield). EI-MS: 358 (M+). $^1$H NMR ($CDCl_3$) δ 6.98 (s, 1H), 6.90 (dd, 1H), 5.52 (d, 1H), 1.15 (d, 1H), 2.22 (s, 1H), 2.19 (s, 1H), 2.11 (s, 1H), 2.10 (s, 1H), 2.09 (s, 1H), 2.08 (s, 1H).

Example 21

Preparation of 2-bromo-3-methyl-4-cyclohexylthiophene: To an icebath-chilled solution of 3-methyl-4-cyclohexylthiophene (10 g, 55.55 mmol) in DMF (60 mL) was added solid N-bromosuccinimide (9.89 g, 55.55 mmol). After addition, the mixture was allowed to warm to room temperature and was stirred for about 1 hr at which point HPLC analysis indicated the reaction was complete. The product mixture was poured into 200 mL of cold water and the aqueous phase was extracted with ether (3×125 mL). The combined ether extracts were washed with water (3×250 mL) and brine (1×200 mL), then passed through a cone of DRIERITE. Solvent was removed by rotary evaporation to afford the crude product 2-bromo-3-methyl-4-cyclohexylthiophene (13.6 g, 94%) as a light amber oil which was judged to be of greater than 95% purity product. $^1$H NMR (CDCl$_3$) δ 6.88 (s, 1, ArH), 2.53 (m, 1, cyclohexylmethine) 2.19 (s, 3,ArCH$_3$), 1.9 and 1.35 ppm (m, 10, cyclohexyls).$^{13}$C NMR 147.81, 135.93, 118.32, 109.44 (thiophene carbons), 39.27, 33.55, 26.86, 26.24 and 13.73 (aliphatic carbons). 2D NMR confirmed that the bromine was bonded to the carbon adjacent to the 3-methyl substituent.

Example 22

Preparation of 2-formyl-3-methyl-4-cyclohexylthiophene: To a solution of 3-methyl-4-cyclohexylthiophene (3 g, 17 mmol) in DMF (10 mL) was added 10 mL of a solution prepared from DMF and POCl$_3$ (4:1, v:v). The temperature was maintained at about 0° C. during the addition. The reaction mixture was then stirred overnight at room temperature, and poured into ice water. After neutralization with 25% NaOH solution to pH~8, the product was extracted with dichloromethane. The solvent was evaporated to afford the crude product 2-formyl-3-methyl-4-cyclohexylthiophene as a solid which was purified by column chromatography (dichloromethane-petroleum ether (1:3)) (2.85 g, yield: 83%). $^1$H NMR (CDCl$_3$) δ 10.07 (s, 1, CHO), 7.28 (s, 1, thienyl-H), 2.58 (m,1,cyclohexyl methane), 2.53 (s, 3,CH$_3$), 1.89 and 1.37 m, 10, cyclohexyl).

Example 23

Preparation of 5-bromo-3-methyl-4-cyclohexyl-2-formylthiophene: To a solution of 2-formyl-3-methyl-4-cyclohexylthiophene (4.1 g, 20 mmol, See Example 22) in 30 mL of a mixture prepared from acetic acid and chloroform (1:1), was added solid N-bromosuccinimide (5.3 g, 30 mmol) slowly in portions at 0° C. The reaction mixture was then stirred overnight at room temperature, poured into water, and extracted repeatedly with dichloromethane. The combined organic layers were washed with saturated NaHCO$_3$ and brine solutions, and dried over anhydrous Na$_2$SO$_4$. After the solvent was removed by rotary evaporation, the remaining solid was purified by column chromatography using silica gel and a dichloromethane-petroleum ether (2:3) as eluant. The solvent was removed by rotary evaporation yielding 3.3 g white solid (57%). $^1$H NMR (CDCl$_3$) δ 9.97 (s, 1, CHO), 2.88 (m, 1,cyclohexyl methane), 2.59 (s, 3,CH$_3$), 1.87 and 1.34 m, 10, cyclohexyl)

Example 24

Preparation of 3-methyl-4-cyclohexylthiophene-2-boryl pinacolate: 2-bromo-3-methyl-4-cyclohexylthiophene (5 g, 19.2 mmol) was dissolved in 30 ml of anhydrous THF. Magnesium turnings (0.55 g, 23 mmol) were added and then the mixture was refluxed for 4 hours to form the corresponding Grignard reagent. A solution of isopropoxypinacolato borane (5.0 g, 26.9 mmole) was added dropwise to the Grignard reagent at −78° C. The mixture was stirred overnight, and then saturated NH$_4$Cl solution (100 mL) was added. The organic layer was separated, dried over anhydrous Na$_2$SO$_4$, and the solvent was removed in vacuo. The reside was subjected to column chromatography to afford the purified product 3-methyl-4-cyclohexylthiophene-2-boryl pinacolate (3.0 g, 51%) as a white solid. $^1$H NMR (CDCl$_3$) δ 7.20 (s, 1H thienyl-H), 2.54 (m, 1H, cyclohexyl methine), 2.42 (s, 3H, CH$_3$), 1.88 and 1.34 (m, 10H, cyclohexyl) and 1.35 ppm (s, 12H, pinacol methyls).

Example 25

Preparation of 2-formyl-3-methyl4-cyclohexylthiophene dimer: 5-bromo-3-methyl-4-cyclohexyl-2-formylthiophene (1.5 g, 5.2 mmol), 3-methyl-4-cyclohexylthiophene-2-boryl pinacolate (1.9 g, 6.24 mmol) and Bu$_4$NBr (33 mg, 0.1 mmol) were added to a 100 ml flask. The mixture of solids was evacuated for 2 hours, then dissolved in dry toluene (30 ml) under argon with stirring. Tetrakis(triphenylphosphine)palladium (100 mg, 0.09 mmol) was added and the solution was heated to 95° for 16 hours. Afterwards, an additional aliquot of boronate (0.5 g) and tetrakis(triphenylphosphine)palladium (50 mg) were added. The reaction was checked, after stirring an additional 20 hours, and found to be complete. The mixture was poured into a saturated solution of ammonium chloride, and extracted with toluene (3×20 mL). The combined organic layers were washed with brine and dried over anhydrous Na$_2$SO$_4$. After the solvent was removed by rotary evaporation. The remaining oil was purified by column chromatography (CH$_2$Cl$_2$:petroleum ether, 2:3) to afford the product 2-formyl-3-methyl-4-cyclohexylthiophene dimer as a yellow solid (1.5 g, 75%). $^1$H NMR (CDCl$_3$) δ 10.08 (s, 1, CHO), 7.01 (s, 1,thienyl-H), 2.67 (m,1,cyclohexyl methane), 2.65 (s, 3,CH$_3$), 2.52 (m,1,cyclohexyl methane), 2.07 (s, 3,CH$_3$), 1.78 and 1.31 (m, 20, cyclohexyl). $^{13}$C NMR (CDCl$_3$) δ 182.5, 148.3, 147.9, 146.5, 140.4, 138.2, 136.7, 128.6, 119.4, 39.7, 38.8, 33.8, 31.3, 27.1, 26.9, 26.3, 25.9, 14.01, 13.3.

Example 26

Preparation of 2-vinyl-3-methyl-4-cyclohexylthiophene dimer: To a solution of methyltriphenylphosphonium bromide (4.983 g, 13.96 mmol) in ether at 0° C. was added dropwise 1.6 M n-BuLi solution in hexane (8.7 ml, 13.96 mmol). The solution was stirred at 0° C. for 40 min and then was warmed to room temperature. A solution of 2-formyl-3-methyl-4-cyclohexylthiophene dimer (2.7 g, 6.98 mmol) in a minimum of ether was added. The solution was stirred overnight. The reaction mixture was then diluted with ether and washed with water and brine, and dried over MgSO$_4$. The solvent was removed in vacuo and the crude product was purified by column chromatography using hexane as the eluant to afford 2-vinyl-3-methyl-4-cyclohexylthiophene dimer 1.32 g (50% yield) as a white solid. $^1$H NMR (CDCl$_3$) δ 6.98 (s, 1H), 6.90 (dd, 1H), 5.52 (d, 1H), 1.15 (d, 1H), 2.22 (s, 1H), 2.19 (s, 1H), 2.11 (s, 1H), 2.10 (s, 1H), 2.09 (s, 1H), 2.08 (s, 1H). $^{13}$C NMR (CDCl$_3$) δ 147.93, 146.37, 137.41, 136.09, 134.78, 129.97, 128.44, 127.57, 118.61, 112.7, 40.07, 38.86, 33.74, 31.37, 27.19, 26.91, 26.30, 26.12, 13.61, 13.33.

The structures of thiophene derivatives discussed in Examples 12-26 are gathered in Table 4.

TABLE 4

THIOPHENE DERIVATIVES

| Example No. | Chemical Name | Structure |
|---|---|---|
| 12 | 3,4-dimethylthiophene | 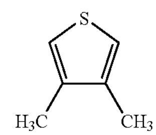 |
| 13 | 2-bromo-3,4-dimethylthiophene | 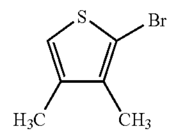 |
| 14 | 2,5-dibromo-3,4-dimethylthiophene | 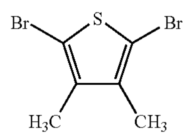 |
| 15 | 3,4-dimethylthiophene dimer | 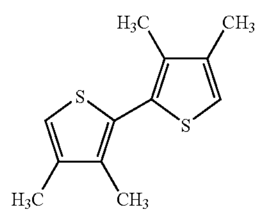 |
| 16 | 3,4-dimethylthiophene trimer | 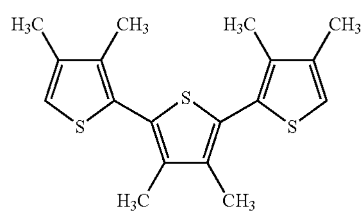 |
| 17 | 2-formyl-3,4-dimethylthiophene dimer | 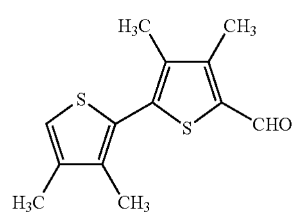 |
| 18/19 | 2-formyl-3,4-dimethylthiophene trimer | 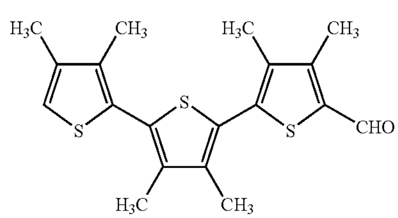 |

TABLE 4-continued

THIOPHENE DERIVATIVES

| Example No. | Chemical Name | Structure |
| --- | --- | --- |
| 20 | 2-vinyl-3,4-dimethylthiophene trimer | 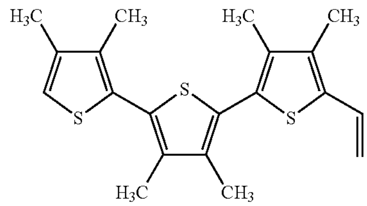 |
| 21 | 2-bromo-3-methyl-4-cyclohexylthiophene | 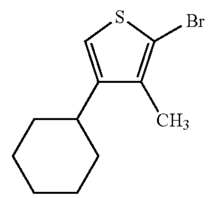 |
| 22 | 2-formyl-3-methyl-4-cyclohexylthiophene | 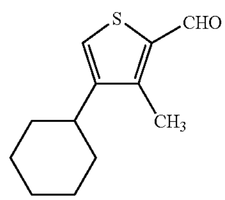 |
| 23 | 5-bromo-3-methyl-4-cyclohexyl-2-formylthiophene | 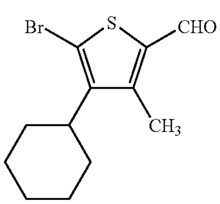 |
| 24 | 3-methyl-4-cyclohexylthiophene-2-boryl pinacolate | 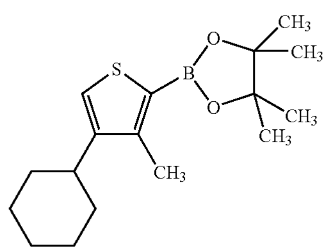 |
| 25 | 2-formyl-3-methyl-4-cyclohexylthiophene dimer | 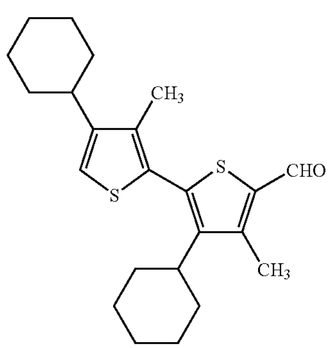 |

TABLE 4-continued

THIOPHENE DERIVATIVES

| Example No. | Chemical Name | Structure |
|---|---|---|
| 26 | 2-vinyl-3-methyl-4-cyclohexylthiophene dimer | 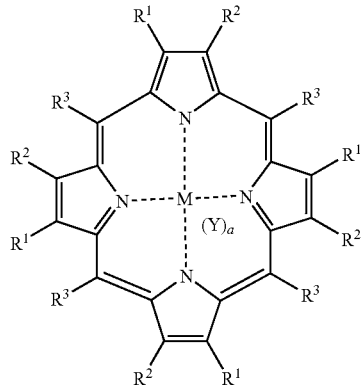 |

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. A composition comprising heterocyclic structure I

I wherein M is a divalent, trivalent or tetravalent metal ion; "a" is 0, 1, 2, or a non-zero fraction having a value between 0 and 1; Y is independently at each occurrence a charge balancing counterion; $R^1$ and $R^2$ are independently at each occurrence a hydrogen, a halogen, a $C_1$-$C_{20}$ aliphatic radical, a $C_3$-$C_{20}$ cycloaliphatic radical, a $C_2$-$C_{20}$ aromatic radical, or $R^1$ and $R^2$ may together form a divalent aliphatic radical, a divalent cycloaliphatic radical, or a divalent aromatic radical; $R^3$ is independently at each occurrence an organic radical having structure II

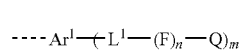

II wherein $Ar^1$ is a $C_2$-$C_{50}$ aromatic radical; $L^1$ is a $C_1$-$C_2$-aliphatic radical, a $C_3$-$C_{20}$ cycloaliphatic radical, or a $C_2$-$C_{20}$ aromatic radical; F is independently at each occurrence a structural unit derived from an olefin monomer of formula III,

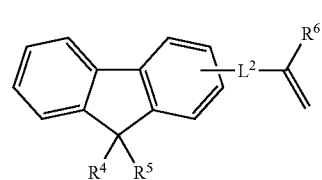

III $R^4$ and $R^5$ are independently hydrogen, $C_1$-$C_{20}$ aliphatic radical, a $C_3$-$C_{20}$ cycloaliphatic radical, or a $C_2$-$C_{20}$ aromatic radical; $L^2$ is a bond, a $C_1$-$C_{20}$ aliphatic radical, a $C_3$-$C_{20}$ cycloaliphatic radical, or a $C_2$-$C_{20}$ aromatic radical; and $R^6$ is hydrogen, halogen, a $C_1$-$C_{20}$ aliphatic radical, a $C_3$-$C_{20}$ cycloaliphatic radical, or a $C_2$-$C_{20}$ aromatic radical;

"n" is independently at each occurrence an integer from 1 to 200;

Q is independently at each occurrence a hydrogen, a halogen, a $C_1$-$C_{20}$ aliphatic radical, a $C_3$-$C_{20}$ cycloaliphatic radical, or a $C_2$-$C_{20}$ aromatic radical; and "m" is independently at each occurrence an integer from 1 to 10.

2. The composition according to claim 1, wherein "a" is 0, and M is selected from the group consisting of $Pd^{2+}$ and $Pt^{2+}$.

3. The composition according to claim 1, wherein "a" is 0, and M is $Pt^{2+}$.

4. The composition according to claim 1, wherein "a" is 0, and M is $Pd^{2+}$.

5. The composition according to claim 1, wherein "a" is 0; M is selected from the group consisting of $Pd^{2+}$ and $Pt^{2+}$; $R^1$ and $R^2$ are H; $Ar^1$ is an aromatic radical of formula XII;

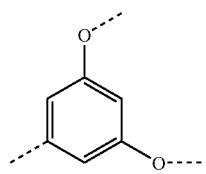

XII $L^1$ is a divalent aliphatic radical having structure XIII;

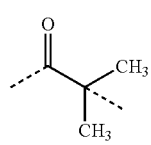

XIII

F is a moiety having structure XIV

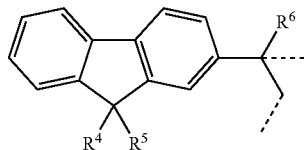

XIV wherein $R^4$ and $R^5$ are independently at each occurrence hydrogen, a $C_1$-$C_{20}$ aliphatic radical, a $C_3$-$C_{20}$ cycloaliphatic radical, or a $C_2$-$C_{20}$ aromatic radical, and $R^6$ is independently at each occurrence a hydrogen, a halogen, a $C_1$-$C_{20}$ aliphatic radical, a $C_3$-$C_{20}$ cycloaliphatic radical, or a $C_2$-$C_{20}$ aromatic radical;

"n" is independently at each occurrence an integer from 2 to 10;

Q is Br; and

"m" is 1 or 2.

6. The composition according to claim 1, wherein "a" is 0; M is selected from the group consisting of $Pd^{2+}$ and $Pt^{2+}$; $R^1$ and $R^2$ are H; $Ar^1$ is an aromatic radical selected from the group consisting of divalent aromatic radicals XI and XII;

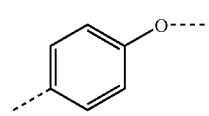

XI

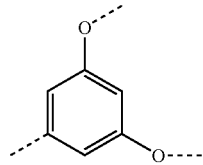

XII $L^1$ is a divalent aliphatic radical having structure XIII;

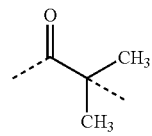

XIII

F is a moiety having structure XV

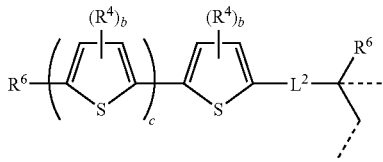

XV wherein $R^4$ is independently at each occurrence hydrogen, a $C_1$-$C_{20}$ aliphatic radical, a $C_3$-$C_{20}$ cycloaliphatic radical, or a $C_2$-$C_{20}$ aromatic radical; $L^2$ is a bond, a $C_1$-$C_{20}$ aliphatic radical, a $C_3$-$C_{20}$ cycloaliphatic radical, or a $C_2$-$C_{20}$ aromatic radical; and $R^6$ is independently at each occurrence a halogen, a $C_1$-$C_{20}$ aliphatic radical, a $C_3$-$C_{20}$ cycloaliphatic radical, or a $C_2$-$C_{20}$ aromatic radical;

"b" is independently at each occurrence 0, 1, or 2;

"c" is a number from 0 to 10;

"n" is independently at each occurrence an integer from 2 to 10;

Q is Br; and

"m" is 1 or 2.

7. The composition according to claim 1, said composition having a number average molecular weight in a range from 1000 grams per mole to 500,000 grams per mole.

8. The composition according to claim 1, said composition having a number average molecular weight in a range from 1000 grams per mole to 25,000 grams per mole.

9. The composition according to claim 1, said composition having a number average molecular weight in a range from 2000 grams per mole to 10,000 grams per mole.

10. The composition according to claim 1, wherein the group Q is a $C_9$ cycloaliphatic radical having structure XVI

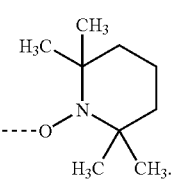

XVI

11. An organic phosphor comprising heterocyclic structure I

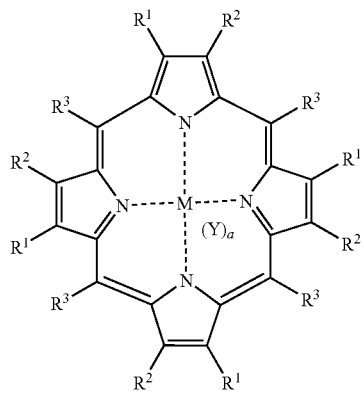

wherein M is a divalent, trivalent or tetravalent metal ion; "a" is 0, 1, 2, or a non-zero fraction having a value between 0 and 1; Y is independently at each occurrence a charge balancing counterion; R1 and R2 are independently at each occurrence a hydrogen, a halogen, a C1-C20 aliphatic radical, a C3-C20 cycloaliphatic radical, a C2-C20 aromatic radical, or R1 and R2 may together form a divalent aliphatic radical, a divalent cycloaliphatic radical, or a divalent aromatic radical; R3 is independently at each occurrence an organic radical having structure II

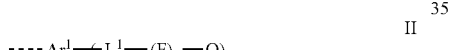

wherein Ar1 is a C2-C50 aromatic radical; L1 is a C1-C20 aliphatic radical, a C3-C20 cycloaliphatic radical, or a C2-C20 aromatic radical; F is independently at each occurrence a structural unit derived from an olefin monomer of formula III,

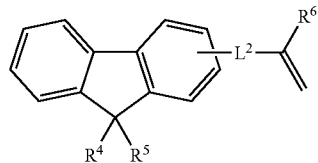

$R^4$ and $R^5$ are independently hydrogen, $C_1$-$C_{20}$ aliphatic radical, a $C_3$-$C_{20}$ cycloaliphatic radical, or a $C_2$-$C_{20}$ aromatic radical; $L^2$ is a bond, a $C_1$-$C_{20}$ aliphatic radical, a $C_3$-$C_{20}$ cycloaliphatic radical, or a $C_2$-$C_{20}$ aromatic radical; and $R^6$ is hydrogen, halogen, a $C_1$-$C_{20}$ aliphatic radical, a $C_3$-$C_{20}$ cycloaliphatic radical, or a $C_2$-$C_{20}$ aromatic radical;

"n" is independently at each occurrence an integer from 1 to 200;

Q is independently at each occurrence a hydrogen, a halogen, a $C_1$-$C_{20}$ aliphatic radical, a $C_3$-$C_{20}$ cycloaliphatic radical, or a $C_2$-$C_{20}$ aromatic radical; and "m" is independently at each occurrence an integer from 1 to 10.

12. The organic phosphor according to claim 11, wherein "a" is 0, and M is selected from the group consisting of $Pd^{2+}$ and $Pt^{2+}$.

13. The organic phosphor according to claim 11, wherein "a" is 0, and M is $Pt^{2+}$.

14. The organic phosphor according to claim 11, wherein "a" is 0, and M is $Pd^{2+}$.

15. The organic phosphor according to claim 11, wherein "a" is 0; M is selected from the group consisting of $Pd^{2+}$ and $Pt^{2+}$; $R^1$ and $R^2$ are H; $Ar^1$ is an aromatic radical of formula XII;

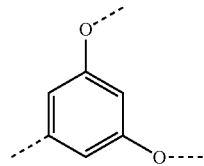

$L^1$ is a divalent aliphatic radical having structure XIII;

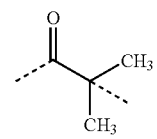

F is a moiety having structure XIV

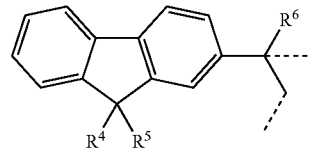

wherein $R^4$ and $R^5$ are independently at each occurrence hydrogen, a $C_1$-$C_{20}$ aliphatic radical, a $C_3$-$C_{20}$ cycloaliphatic radical, or a $C_2$-$C_{20}$ aromatic radical, and $R^6$ is independently at each occurrence a hydrogen, a halogen, a $C_1$-$C_{20}$ aliphatic radical, a $C_3$-$C_{20}$ cycloaliphatic radical, or a $C_2$-$C_{20}$ aromatic radical;

"n" is independently at each occurrence an integer from 2 to 10;

Q is Br; and

"m" is 1 or 2.

16. The organic phosphor according to claim 11, wherein "a" is 0; M is selected from the group consisting of $Pd^{2+}$ and $Pt^{2+}$; $R^1$ and $R^2$ are H; $Ar^1$ is an aromatic radical selected from the group consisting of divalent aromatic radicals XI and XII;

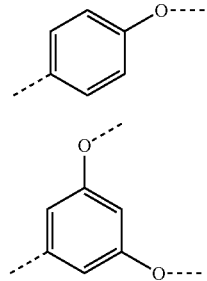

XI

XII $L^1$ is a divalent aliphatic radical having structure XIII;

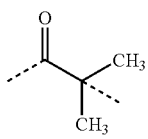

XIII

F is a moiety having structure XV

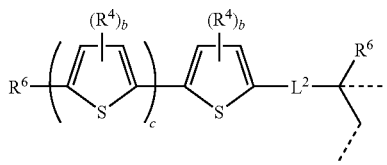

XV wherein $R^4$ is independently at each occurrence hydrogen, a $C_1$-$C_{20}$ aliphatic radical, a $C_3$-$C_{20}$ cycloaliphatic radical, or a $C_2$-$C_{20}$ aromatic radical, and $R^6$ is independently at each occurrence a halogen, a $C_1$-$C_{20}$ aliphatic radical, a $C_3$-$C_{20}$ cycloaliphatic radical, or a $C_2$-$C_{20}$ aromatic radical; $L^2$ is a bond, a $C_1$-$C_{20}$ aliphatic radical, a $C_3$-$C_{20}$ cycloaliphatic radical, or a $C_2$-$C_{20}$ aromatic radical;

"b" is independently at each occurrence 0, 1, or 2;

"c" is a number from 0 to 10;

"n" is independently at each occurrence an integer from 2 to 10;

Q is Br; and

"m" is 1 or 2.

17. The organic phosphor according to claim 11, said composition having a number average molecular weight in a range from 1000 grams per mole to 500,000 grams per mole.

18. The organic phosphor according to claim 11, said composition having a number average molecular weight in a range from 2000 grams per mole to 10,000 grams per mole.

19. The organic phosphor according to claim 11, wherein the group Q is a $C_9$ cycloaliphatic radical having structure XVI

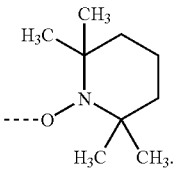

XVI

20. The organic phosphor according to claim 11, wherein the phosphor is characterized by a red phosphorescence.

* * * * *

UNITED STATES PATENT AND TRADEMARK OFFICE
CERTIFICATE OF CORRECTION

PATENT NO.       : 7,663,301 B2
APPLICATION NO.  : 11/326949
DATED            : February 16, 2010
INVENTOR(S)      : Litz et al.

It is certified that error appears in the above-identified patent and that said Letters Patent is hereby corrected as shown below:

In Column 5, Line 1, delete "terahydrofuranyl," and insert -- tetrahydrofuranyl, --, therefor.

In Column 5, Line 4, delete "4-HOCH$_2$C$_6$H$_{10}$O—)," and insert -- 4-HOCH$_2$C$_6$H$_{10}$—), --, therefor.

In Column 5, Line 5, delete "4-HSCH$_2$C$_6$H$_{10}$O—)," and insert -- 4-HSCH$_2$C$_6$H$_{10}$—), --, therefor.

In Column 6, Line 47, delete "(—(CH$_2$)$_3$CHcyclohexyl-)" and insert -- (—(CH$_2$)$_3$CH-) cyclohexyl --, therefor.

In Column 9, Line 16, delete "L" and insert -- L$^2$ --, therefor.

In Column 9, Lines 61-64, delete " 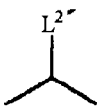 " and insert -- 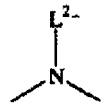 --, therefor.

In Column 18, Line 6, delete "M=Pd," and insert -- M=Pd$^{2+}$ --, therefor.

In Column 21, Line 52, delete "Exanple 11" and insert -- Example 11 --, therefor.

In Column 32, Line 38, in Claim 1, delete "C$_1$-C$_2$-" and insert -- C$_1$-C$_{20}$ --, therefor.

In Column 35, Line 25, in Claim 11, delete "R1 and R2" and insert -- R$^1$ and R$^2$ --, therefor.

In Column 35, Line 27, in Claim 11, delete "C1-C20" and insert -- C$_1$-C$_{20}$ --, therefor.

In Column 35, Line 27, in Claim 11, delete "C3-C20" and insert -- C$_3$-C$_{20}$ --, therefor.

In Column 35, Line 28, in Claim 11, delete "C2-C20" and insert -- C$_2$-C$_{20}$ --, therefor.

In Column 35, Line 30, in Claim 11, delete "R3" and insert -- R$^3$ --, therefor.

In Column 35, Line 39, in Claim 11, delete "Ar1 is a C2-C50" and insert -- Ar$^1$ is a C$_2$-C$_{50}$ --, therefor.

In Column 35, Line 39, in Claim 11, delete "L1 is a C1-C20" and insert -- L$^1$ is a C$_1$-C$_{20}$ --, therefor.

In Column 35, Line 40, in Claim 11, delete "C3-C20" and insert -- C$_3$-C$_{20}$ --, therefor.

CERTIFICATE OF CORRECTION (continued)
U.S. Pat. No. 7,663,301 B2

In Column 35, Line 41, in Claim 11, delete "C2-C20" and insert -- $C_2$-$C_{20}$ --, therefor.

In Column 35, Line 28, in Claim 11, delete "R1 and R2" and insert -- $R^1$ and $R^2$ --, therefor.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,663,301 B2 Page 1 of 1
APPLICATION NO. : 11/326949
DATED : February 16, 2010
INVENTOR(S) : Litz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 557 days.

Signed and Sealed this

Twenty-eighth Day of December, 2010

David J. Kappos
*Director of the United States Patent and Trademark Office*